US012742708B2

(12) United States Patent
Mizutani et al.

(10) Patent No.: US 12,742,708 B2
(45) Date of Patent: Sep. 22, 2026

(54) GAS DETECTION SYSTEM

(71) Applicant: SINTOKOGIO, LTD., Nagoya (JP)

(72) Inventors: Manase Mizutani, Nagoya (JP); Yoshihisa Suzuki, Nagoya (JP)

(73) Assignee: SINTOKOGIO, LTD., Nagoya (JP)

( * ) Notice: Subject to any disclaimer, the term of this patent is extended or adjusted under 35 U.S.C. 154(b) by 274 days.

(21) Appl. No.: 18/140,187

(22) Filed: Apr. 27, 2023

(65) Prior Publication Data

US 2023/0408379 A1 Dec. 21, 2023

(30) Foreign Application Priority Data

Jun. 16, 2022 (JP) ................................ 2022-097324

(51) Int. Cl.
*G01N 33/00* (2006.01)
*G01N 1/22* (2006.01)
*G01N 1/24* (2006.01)

(52) U.S. Cl.
CPC ......... *G01N 1/2205* (2013.01); *G01N 1/2273* (2013.01); *G01N 1/24* (2013.01); *G01N 33/0037* (2013.01)

(58) Field of Classification Search
CPC ...... G01N 1/2205; G01N 1/2273; G01N 1/24; G01N 33/0014; G01N 33/0011; G01N 1/40; G01N 1/4077; G01N 33/0019; G01N 33/0044; G01N 2001/4088
USPC ...... 73/863.3, 19.2, 23.2, 23.34, 31.01–31.3, 73/31.07, 863.21, 864.73, 861–861.69, 73/195–271; 95/82–89, 28; 96/101–107, 96/2; 138/33; 219/628, 630
See application file for complete search history.

(56) References Cited

U.S. PATENT DOCUMENTS 5,039,322 A 8/1991 Holzl
8,251,091 B2 * 8/2012 Zolock ...................... G01F 5/00 73/202.5
2003/0012696 A1 1/2003 Millancourt
2013/0199269 A1 * 8/2013 Soers ................ G01N 30/7206 73/31.03

(Continued)

FOREIGN PATENT DOCUMENTS

CN 202485950 U 10/2012
CN 114544272 A * 5/2022

(Continued)

OTHER PUBLICATIONS

Extended European Search Report from EP 23172266.1 dated Jan. 23, 2024.

(Continued)

*Primary Examiner* — Robert R Raevis
(74) *Attorney, Agent, or Firm* — Harness Dickey & Pierce P.L.C.

(57) ABSTRACT

A gas flow path includes: a filter configured to selectively transmit a gas; a tubular member which is provided downstream of the filter and in which an opening area at a downstream end is smaller than an opening area at an upstream end; and a negative pressure generating device which is provided in a stage subsequent to the tubular member and which is configured to suck the gas that has passed through the tubular member. This provides a gas flow path and a gas detection system which can concentrate a detection-target gas species in a real-time manner.

7 Claims, 1 Drawing Sheet

(56) References Cited

U.S. PATENT DOCUMENTS

| | | | |
|---|---|---|---|
| 2017/0248565 | A1 | 8/2017 | Yamada et al. |
| 2017/0248566 | A1 | 8/2017 | Yamada et al. |

FOREIGN PATENT DOCUMENTS

| | | | | |
|---|---|---|---|---|
| JP | S59188553 | A | | 10/1984 |
| JP | 2005181229 | A | | 7/2005 |
| JP | 2015142898 | A | | 8/2015 |
| JP | 2017156346 | A | | 9/2017 |
| JP | 2022512502 | A | | 2/2022 |
| WO | 8602160 | A1 | | 4/1986 |
| WO | 9109307 | | * | 6/1991 |
| WO | 2017051180 | A1 | | 3/2017 |

OTHER PUBLICATIONS

Partial search report from EP Application No. 23172266.1, dated Nov. 7, 2023.

Office Action From Japanese Application No. 2022-097324 dated Feb. 10, 2026.

* cited by examiner

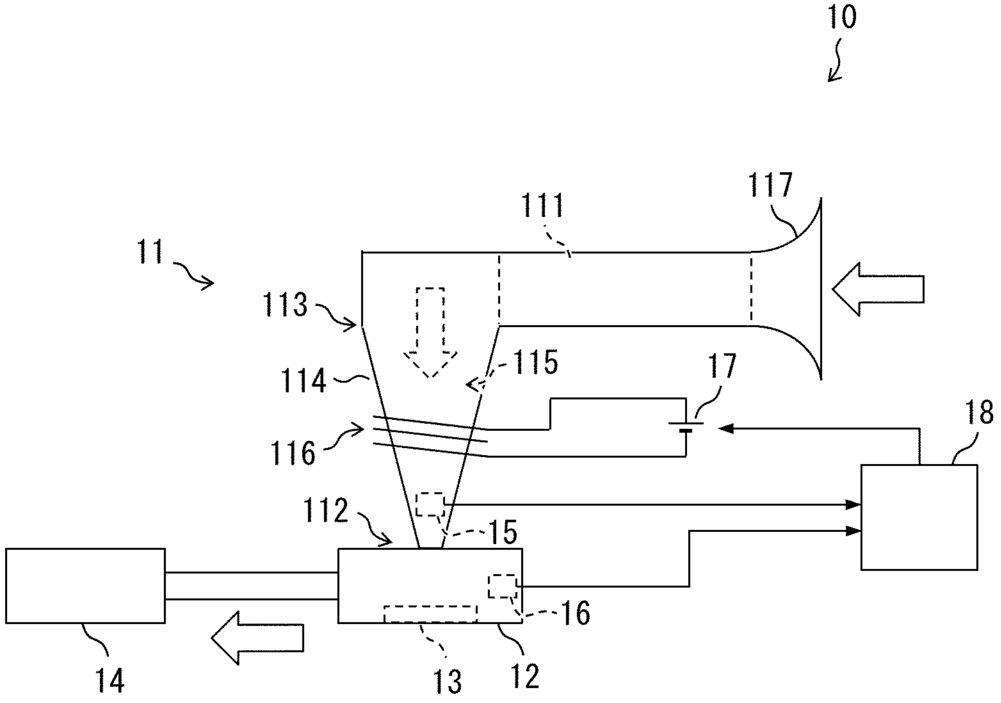
10
11
111
117
113
114
115
17
116
18
112
15
16
14
13
12

GAS DETECTION SYSTEM

This Nonprovisional application claims priority under 35 U.S.C. § 119 on Patent Application No. 2022-097324 filed in Japan on Jun. 16, 2022, the entire contents of which are hereby incorporated by reference.

TECHNICAL FIELD

The present invention relates to a gas flow path and a gas detection system.

BACKGROUND ART

There have been known a variety of methods for detecting a gas species at a relatively high concentration. However, it is difficult to detect a low-concentration gas species that has dispersed in an atmospheric air. For example, a commercially available gas sensor for detecting a specific sulfur gas has a concentration detection limit of the order of ppm.

In a case where a detection-target gas species has a concentration which is lower than a concentration detection limit of a gas sensor, employed is a method in which the gas species is concentrated. In this method, the detection-target gas species is occluded by a filter for a predetermined period of time, and then the gas species occluded by the filter is released from the filter. As a result, the gas species can be concentrated so as to have a concentration that is higher than the concentration detection limit of the gas sensor (see, for example, Patent Literature 1).

CITATION LIST

Patent Literature

[Patent Literature 1]

Japanese Patent Application Publication Tokukai No. 2017-156346

SUMMARY OF INVENTION

Technical Problem

However, in such a conventional method, after a detection-target gas species has been occluded by a filter for a predetermined period of time, the gas species is released from the filter. Thus, the conventional method unfortunately cannot detect a gas species in a real-time manner.

An embodiment of the present invention is achieved in light of the above problem, and it is an object of the embodiment of the present invention to provide a gas flow path and a gas detection system each of which can concentrate, in a real-time manner, a detection-target gas species without occluding the gas species even in a case where the detection-target gas species is at a low concentration.

Solution to Problem

In order to solve the foregoing problem, a gas flow path in accordance with Aspect 1 of the present invention includes: a filter configured to selectively transmit a gas; a tubular member through which the gas having passed through the filter passes and in which an opening area at a downstream end is smaller than an opening area at an upstream end; and a negative pressure generating device which is provided in a stage subsequent to the tubular member and which is configured to suck the gas that has passed through the tubular member.

Advantageous Effects of Invention

An embodiment of the present invention makes it possible to provide a gas flow path and a gas detection system each of which can concentrate, in a real-time manner, a detection-target gas species without occluding the gas species even in a case where the detection-target gas species is at a low concentration.

BRIEF DESCRIPTION OF DRAWINGS

FIG. 1 is a block diagram illustrating a gas detection system in accordance with an embodiment of the present invention.

DESCRIPTION OF EMBODIMENTS

Configuration of Gas Detection System

The following will describe a configuration of a gas detection system 10 in accordance with an embodiment of the present invention with reference to FIG. 1. FIG. 1 is a block diagram illustrating the gas detection system 10. In FIG. 1, outline arrows indicate directions in which gas flows from upstream to downstream.

The gas detection system 10 is a system for detecting a gas, and as illustrated in FIG. 1, includes: a gas flow path 11 in accordance with an aspect of the present invention; a chamber 12 provided downstream of the gas flow path 11; and a gas sensor 13 accommodated in the chamber 12. In such a configuration, with use of the gas flow path 11 in accordance with an aspect of the present invention, a detection-target gas species can be concentrated in a real-time manner, and then, with use of the gas sensor 13 provided downstream of the gas flow path 11, the detection-target gas concentrated can be detected in a real-time manner.

In the present embodiment, the detection-target gas species in the gas detection system 10 is a sulfur-based gas. Note, however, that a gas detectable by the gas detection system 10 may be any gas that the filter 111 described later can selectively transmit. The expression "selectively transmit" herein means to, with use of gas properties, transmit the detection-target gas species and exclude an unnecessary gas. As the gas properties, for example, polarity and a molecular weight can be used. Further, in order to make the gas easily affected by an electromagnetic field that is generated by a coil 116 described later, the gas detectable by the gas detection system 10 preferably contains a polar molecule in which electric charges are unevenly distributed. Examples of such a polar molecule include ammonia, hydrogen sulfide, and ethanol.

Gas Flow Path 11

The gas flow path 11 includes: a filter 111 which selectively transmits a gas; a tubular member 114 through which the gas having passed through the filter 111 passes and in which an opening area at a downstream end 112 is smaller than an opening area at an upstream end 113; and a pump 14 which is provided downstream of the chamber 12 and which discharges air from the gas flow path 11 and the chamber 12. The tubular member 114 is provided downstream of the filter 111. In the gas flow path 11, passage of the gas the tubular member 114 can lead to an increased concentration of the detection-target gas species contained in the gas. Thus, the gas flow path 11 can concentrate, in a real-time manner, the detection-target gas species without occluding the gas species even in a case where the detection-target gas species is at a low concentration. The gas flow path 11 further includes a suction port 117. Through the suction port 117, the gas flow path 11 sucks gas. In addition, the gas flow path 11 may further include a valve (not illustrated) at a downstream end of the filter 111. The valve prevents the filter 111 from coming into the chamber 12. The pump 14 is one example of a negative pressure generating device and constitutes a terminal end of the gas flow path 11. The negative pressure generating device is provided in a stage subsequent to the tubular member 114 and sucks the gas which has passed through the tubular member 114. A specific configuration of the pump 14 will be described later.

Filter 111

The filter 111 is connected with the suction port 117 and selectively transmits the gas that has been sucked from the suction port 117. In the present embodiment, the filter 111 is made of a metal organic framework (MOF) in which metal ions are cross-linked three-dimensionally and periodically by organic ligands, and the organic ligands each have an acidic functional group. The metal organic framework is herein also referred to as a porous coordination polymer (PCP). Adjustment of a pore diameter of the metal organic framework allows the filter 111 to separate the gas species which the filter 111 transmits from a gas species which the filter 111 does not transmit. Further, in a case where the ligand has an acidic functional group, the filter 111 occludes a basic gas species and transmits an acidic gas species. Thus, the filter 111 transmits a sulfur-based gas which is a detection target and occludes a basic gas species which is unnecessary for detection. Note, however, that the organic ligand may have a basic functional group. In a case where the organic ligand has a basic functional group, the filter 111 occludes an acidic gas species and transmits a basic gas species. Such a configuration allows the filter 111 to separate gas species depending on polarities of the gas species as well as separate gas species in accordance with a pore diameter of the metal organic framework. Thus, the gas flow path 11 can appropriately exclude a gas species which is not a detection target. Note, however, that the filter 111 can be any filter which can selectively transmit the detection-target gas, and the filter 111 can be selected as appropriate depending on the detection-target gas species.

The gas species that has been occluded by the filter 111 can be removed by the following method. That is, the gas species adsorbed can be removed by increasing a temperature of the filter 111 in a state in which while operations of the gas sensor 13, a first pressure sensor 15, a second pressure sensor 16, a power source 17, and a control section 18 are stopped, the pump 14 is operated. This makes it possible to reuse the filter 111 without replacing the filter 111. Thus, it is possible to save the effort of and cut cost for replacing the filter 111.

Tubular Member 114

The tubular member 114 is provided downstream of the filter 111, and is the tubular member in which the opening area at the downstream end 112 is smaller than the opening area at the upstream end 113. The opening area at the downstream end 112 refers to an area of an opening at the downstream end 112, and the opening area at the upstream end 113 refers to an area of an opening at the upstream end 113. In the present embodiment, the opening at the downstream end 112 and the opening at the upstream end 113 each have a circular shape. That is, in the present embodiment, the tubular member 114 has a cylindrical shape.

In the present embodiment, the tubular member 114 has an inner diameter (diameter of an inner space 115) that is set to continuously decrease from the upstream end 113 toward the downstream end 112. That is, the present embodiment employs the tubular member 114 having a tapered shape such that the inner space 115 smoothly tapers from the upstream end 113 toward the downstream end 112. In a case where gas which has been supplied from the upstream end 113 having a larger opening area is discharged from the downstream end 112 having a smaller opening area, the above configuration can reduce a disorder that may occur in a flow of the gas. Thus, the gas flow path 11 can reduce a pressure loss in the gas while concentrating the detection-target gas species.

Coil 116

The gas flow path 11 further includes the coil 116 that is disposed so as to have an axis along an axial direction of the tubular member 114 and so as to surround the tubular member 114. Supplying a driving current to the coil 116 causes an electromagnetic field around the coil 116. Especially in the vicinity of the axis of the coil 116, the electromagnetic field is generated along a direction of the axis of the coil 116. The driving current is supplied by the power source 17 described later. According to such a configuration, the electromagnetic field generated by the coil 116 interacts with the gas species, so that the gas which has been supplied from the upstream end 113 of the tubular member 114 to the inner space 115 of the tubular member 114 flows toward the downstream end 112 while swirling. Thus, the gas flow path 11 makes it possible to further reduce the pressure loss in the gas.

In the present embodiment, the coil 116 has a helical shape when seen in plan view from an axial direction of the coil 116, and the tubular member 114 and the coil 116 are disposed so as to be coaxial. Such a configuration allows the gas flowing from the upstream end 113 of the tubular member 114 to the downstream end 112 of the tubular member 114 to swirl more neatly. Thus, the gas flow path 11 makes it possible to further reduce the pressure loss in the gas.

Chamber 12

The chamber 12 is provided downstream of the gas flow path 11. The chamber 12 is connected with the downstream end 112 of the tubular member 114 and is provided with a supply port (not illustrated) through which the gas is supplied from the gas flow path 11 and a discharge port (not illustrated) through which the gas is discharged to the pump 14.

Gas Sensor 13

The gas sensor 13 is accommodated in the chamber 12. In the present embodiment, the gas sensor 13 is a gas sensor which can detect a sulfur-based gas. Note, however, that the gas sensor 13 can be any gas sensor which can detect the detection-target gas species. Examples of such a gas sensor include gas sensors of a semiconductor type, of an electrochemical type, and of a crystal oscillator type.

Pump 14

The present embodiment employs the pump 14 as a negative pressure generating device. The pump 14 is provided downstream of the chamber 12 and discharges air from the gas flow path 11 and the chamber 12. In the present embodiment, the pump 14 can be of any type as long as air can be discharged from the gas flow path 11 and the chamber 12, and the type of the pump 14 can be selected as appropriate in accordance with a discharge capacity. It is possible to use, for example, a diaphragm pump, a rotary pump, an oil diffusion pump, or a turbomolecular pump. The pump 14 discharges the air from the gas flow path 11 and the chamber 12 so that the gas flow path 11 and the chamber 12 each have a pressure lower than an atmospheric pressure (that is, a negative pressure).

The gas detection system 10 of the present embodiment further includes the first pressure sensor 15, the second pressure sensor 16, the power source 17, and the control section 18. The first pressure sensor 15 can detect a first pressure, which is a pressure inside the tubular member 114, and the second pressure sensor 16 can detect a second pressure, which is a pressure inside the chamber 12. In such a configuration, the driving current for the coil 116 is set in accordance with a difference between the first pressure and the second pressure, and therefore it is possible to set the driving current so that the pressure loss in the gas is reduced.

First Pressure Sensor 15 and Second Pressure Sensor 16

The first pressure sensor 15 is accommodated in the tubular member 114. The first pressure sensor 15 detects the first pressure, which is a pressure inside the tubular member 114, and supplies first pressure information indicative of the first pressure to the control section 18. The second pressure sensor 16 is accommodated in the chamber 12. The second pressure sensor 16 detects the second pressure, which is a pressure inside the chamber 12, and supplies second pressure information indicative of the second pressure to the control section 18. Each of the type of the first pressure sensor 15 and the type of the second pressure sensor 16 can be any type as long as a negative pressure can be measured. The type can be selected as appropriate by a person skilled in the art.

Power Source 17

The power source 17 is configured to supply a driving current to the coil 116. The power source 17 acquires a control signal generated by the control section 18 described later and supplies a driving current to the coil 116 on the basis of the control signal. The power source 17 is preferably a constant direct current source. Note, however, that the power source 17 is not limited to this and can be any power source which is configured to be able to supply, to the coil 116, a driving current that allows the coil 116 to generate a desired electromagnetic field.

Control Section 18

The control section 18 is configured to set a driving current in accordance with the difference between the first pressure and the second pressure. The control section 18 acquires: the first pressure information that is supplied from the first pressure sensor 15; and the second pressure information that is supplied from the second pressure sensor 16. The control section 18 then calculates the difference between the first pressure and the second pressure and sets the driving current in accordance with the difference. Here, the control section 18 refers to a predetermined correlation between the difference and the driving current and sets, on the basis of the correlation, a driving current corresponding to the difference. The correlation is preferably set such that the difference positively correlates with the driving current. The correlation may be expressed in a lookup table or may be represented by a function (for example, a linear function). Further, the control section 18 supplies the power source 17 with a control signal for controlling the power source 17 so as to allow the power source 17 to supply the coil 116 with the driving current thus set. Part of or all of the functions of the control section 18 may be realized by hardware such as an integrated circuit (IC chip) or may be realized by software. In the present embodiment, the control section 18 is realized by software. In this case, the control section 18 has functions realized by, for example, a computer which executes a program which is software.

Operation

Now, the following will describe the gas detection system 10 in accordance with the present embodiment which is constituted by the above-described configurations.

First, air is discharged from the gas flow path 11 and the chamber 12 by driving the pump 14 so that a gas to be sucked and to be detected is prevented from mixing with an existing gas in the gas flow path 11 and the chamber 12.

The pump 14 is kept driven, and the inside of the gas flow path 11 and the inside of the chamber 12 are kept under a negative pressure. This makes it possible to suck, from the suction port 117, the gas to be detected. The gas sucked is selectively transmitted by the filter 111 and then flows into the tubular member 114 that is surrounded by the coil 116.

At that time, the coil 116 surrounding the tubular member 114 is supplied, from the power source 17, with a driving current set by the control section 18 on the basis of information on the pressures detected by the first pressure sensor 15 and the second pressure sensor 16. Thus, the coil 116 generates an electromagnetic field around the tubular member 114.

This electromagnetic field which is being generated interacts with the gas that has flowed into the tubular member 114, so that the gas which is flowing downstream by the negative pressure generated by the pump 14 more neatly flows toward the downstream end 112 while swirling. This swirling reduces a pressure loss.

The gas species of the gas which has flowed into the chamber 12 from the downstream end 112 is detected by the gas sensor 13 provided in the chamber 12.

The gas which has been detected by the gas sensor 13 is discharged by the pump 14 connected with the chamber 12.

Effects

In light of above, the gas detection system 10 makes it possible to, with use of the gas flow path 11 in accordance with an aspect of the present invention, concentrate a detection-target sulfur-based gas in a real-time manner, and then to, with use of the gas sensor 13 provided downstream of the gas flow path 11, detect, in a real-time manner, the sulfur-based gas concentrated. Thus, for example, detection of a sulfur-based gas that is at a low concentration and that is derived from an agricultural product makes it possible to know a degree of maturity and a state of spoilage of the agricultural product in a real-time manner. This consequently makes it possible to efficiently cultivate, distribute, and preserve agricultural products, leading to decrease of loss of agricultural products.

Aspects of the present invention can also be expressed as follows:

A gas flow path according to Aspect 1 of the present invention includes: a filter configured to selectively transmit a gas; a tubular member through which the gas having passed through the filter passes and in which an opening area at a downstream end is smaller than an opening area at an upstream end; and a negative pressure generating device which is provided in a stage subsequent to the tubular member and which is configured to suck the gas that has passed through the tubular member.

According to the above configuration, it is possible to increase a concentration of a detection-target gas species contained in the gas by causing the gas to pass through the tubular member. Thus, the gas flow path can concentrate, in a real-time manner, the detection-target gas species without occluding the gas species even in a case where the detection-target gas species is at a low concentration.

The gas flow path according to Aspect 2 of the present invention employs, in addition to the configuration of the gas flow path according to Aspect 1, a configuration in which the tubular member has an inner space which smoothly tapers from the upstream end toward the downstream end.

According to the above configuration, in a case where the gas which has been supplied from the upstream end having a larger opening area is discharged from the downstream end having a smaller opening area, it is possible to reduce a disorder that may occur in a flow of the gas. Thus, the gas flow path can reduce a pressure loss in the gas while concentrating the detection-target gas species.

The gas flow path according to Aspect 3 of the present invention employs, in addition to the configuration of the gas flow path according to Aspect 1 or 2, a configuration such that the gas flow path further includes a coil which is disposed so as to have an axis along an axial direction of the tubular member and so as to surround the tubular member.

Supplying a driving current to the coil generates an electromagnetic field around the coil. Especially in the vicinity of the axis of the coil, the electromagnetic field is generated along a direction of the axis of the coil. According to the above configuration, the electromagnetic field generated by the coil interacts with the gas species, so that the gas which has been supplied from the upstream end of the tubular member to the inner space of the tubular member flows toward the downstream end while swirling. Thus, the gas flow path can further reduce the pressure loss in the gas.

The gas flow path according to Aspect 4 of the present invention employs, in addition to the configuration of the gas flow path according to any one of Aspects 1 to 3, a configuration such that: the tubular member has a cylindrical shape; the coil has a helical shape when seen in plan view from an axial direction of the coil; and the tubular member and the coil are disposed so as to be coaxial.

According to the above configuration, it is possible to allow the gas flowing from the upstream end of the tubular member toward the downstream end of the tubular member to swirl more neatly. Thus, the gas flow path can further reduce the pressure loss in the gas.

The gas flow path according to Aspect 5 of the present invention employs, in addition to the configuration of the gas flow path according to any one of Aspects 1 to 4, a configuration such that: the filter is made of a metal organic framework in which metal ions are cross-linked three-dimensionally and periodically by organic ligands; and the organic ligands each have an acidic functional group or basic functional group.

In a case where the organic ligands each have an acidic functional group, the filter occludes a basic gas species and transmits an acidic gas species. In contrast, in a case where the organic ligands each have a basic functional group, the filter occludes an acidic gas species and transmits a basic gas species. According to the above configuration, the filter can separate gas species depending on polarities of the gas species as well as separate the gas species in accordance with a pore diameter of the metal organic framework. Thus, the gas flow path can more appropriately exclude a gas species which is not a detection target.

A gas detection system according to Aspect 6 of the present invention includes: the gas flow path according to any one of Aspect 1 to 5; a chamber provided downstream of the gas flow path; and a gas sensor accommodated in the chamber, the negative pressure generating device being disposed downstream of the chamber and being a pump configured to discharge air from the gas flow path and the chamber.

According to the above configuration, it is possible to, with use of the gas flow path in accordance with an aspect of the present invention, concentrate the detection-target gas species in a real-time manner and then to, with use of the gas sensor provided downstream of the gas flow path, detect, in a real-time manner, the detection-target gas species concentrated.

The gas detection system according to Aspect 7 of the present invention employs, in addition to the configuration of the gas detection system according to Aspect 6, a configuration such that the gas detection system further includes: a first pressure sensor configured to detect a first pressure, which is a pressure inside the tubular member; a second pressure sensor configured to detect a second pressure, which is a pressure inside the chamber; a power source configured to supply a driving current to the coil; and a control section configured to set the driving current in accordance with a difference between the first pressure and the second pressure.

According to the above configuration, the driving current for the coil is set in accordance with a difference between the first pressure and the second pressure, and therefore it is possible to set the driving current so that the pressure loss in the gas is reduced.

The gas detection system according to Aspect 8 of the present invention employs, in addition to the configuration of the gas detection system according to Aspect 6 or 7, a configuration such that the control section sets the driving current such that the difference positively correlates with the driving current.

A large difference between the first pressure and the second pressure means a large pressure loss in the gas. According to the above configuration, the larger the difference between the first pressure and the second pressure is, the more the gas can be caused to swirl strongly. Thus, it is possible to appropriately reduce the pressure loss in the gas.

SUPPLEMENTARY NOTE

The present invention is not limited to the embodiments, but can be altered by a person skilled in the art within the scope of the claims. The present invention also encompasses, in its technical scope, any embodiment derived by combining technical means disclosed in differing embodiments.

The invention claimed is:

1. A gas detection system for detecting a gas species, comprising:

a gas flow path;

a chamber provided downstream of the gas flow path;

a gas sensor accommodated in the chamber; and a negative pressure generating device provided downstream of the chamber, wherein the gas flow path comprises:

a filter configured to selectively transmit a detection-target gas species and exclude an unnecessary gas with use of gas properties; and a tubular member through which the detection-target gas species having passed through the filter passes and in which an opening area at a downstream end is smaller than an opening area at an upstream end, wherein the gas sensor is for detecting the detection-target gas species, and wherein the negative pressure generating device comprises a pump configured to discharge air from the gas flow path and the chamber.

2. The gas detection system according to claim 1, wherein the tubular member has an inner space which smoothly tapers from the upstream end toward the downstream end.

3. A gas detection system comprising:

a gas flow path;

a chamber provided downstream of the gas flow path;

a gas sensor accommodated in the chamber; and a negative pressure generating device provided downstream of the chamber, wherein the gas flow path comprises:

a filter configured to selectively transmit a gas; and a tubular member through which the gas having passed through the filter passes and in which an opening area at a downstream end is smaller than an opening area at an upstream end, and wherein the negative pressure generating device comprises a pump configured to discharge air from the gas flow path and the chamber, wherein the gas detection system detects a gas species containing a polar molecule with an uneven distribution of electric charge, and wherein the gas detection system further comprises a coil which is disposed so as to have an axis along an axial direction of the tubular member and so as to surround the tubular member.

4. The gas detection system according to claim 3, wherein the tubular member has a cone shape;

wherein the coil has a helical shape when seen in plan view from an axial direction of the coil; and wherein the tubular member and the coil are disposed so as to be coaxial.

5. The gas detection system according to claim 3, further comprising:

a first pressure sensor configured to detect a first pressure, which is a pressure inside the tubular member;

a second pressure sensor configured to detect a second pressure, which is a pressure inside the chamber;

a power source configured to supply a driving current to the coil; and a control section configured to set the driving current in accordance with a difference between the first pressure and the second pressure.

6. The gas detection system according to claim 5, wherein the control section sets the driving current such that the difference positively correlates with the driving current.

7. A gas detection system comprising:

a gas flow path;

a chamber provided downstream of the gas flow path;

a gas sensor accommodated in the chamber; and a negative pressure generating device provided downstream of the chamber, wherein the gas flow path comprises:

a filter configured to selectively transmit a gas; and a tubular member through which the gas having passed through the filter passes and in which an opening area at a downstream end is smaller than an opening area at an upstream end, and wherein the negative pressure generating device comprises a pump configured to discharge air from the gas flow path and the chamber, wherein the filter is made of a metal organic framework in which metal ions are cross-linked three-dimensionally and periodically by organic ligands, and wherein the organic ligands each have an acidic functional group or basic functional group.

* * * * *